United States Patent [19]
King et al.

[11] Patent Number: 6,083,252
[45] Date of Patent: Jul. 4, 2000

[54] TECHNIQUES FOR ADJUSTING THE LOCUS OF EXCITATION OF ELECTRICALLY EXCITABLE TISSUE

[75] Inventors: Gary W. King, Fridley; Michael D. Baudino, Coon Rapids, both of Minn.

[73] Assignee: Medtronic, Inc., Minneapolis, Minn.

[21] Appl. No.: 09/312,470

[22] Filed: May 17, 1999

Related U.S. Application Data

[60] Division of application No. 08/814,432, Mar. 10, 1997, Pat. No. 5,925,070, and a continuation-in-part of application No. 08/627,578, Apr. 4, 1996, abandoned, and a continuation-in-part of application No. 08/637,361, Apr. 25, 1996, Pat. No. 5,713,922.

[51] Int. Cl.$^7$ ..................................................... A61N 1/05
[52] U.S. Cl. ................................................. 607/70; 607/67
[58] Field of Search .................................. 607/66, 67, 70, 607/46

[56] References Cited

U.S. PATENT DOCUMENTS 5,501,703  3/1996  Holsheimer et al. ...................... 607/46

OTHER PUBLICATIONS

Struijk et al, "Transverse Tripolar Spinal Cord Stimulation: Theoretical performance of a dual channel system," 273–279, Medical & Biological Engineering & Computing, Jul. 1996.

*Primary Examiner*—William E Kamm
*Assistant Examiner*—George R. Evanisko
*Attorney, Agent, or Firm*—Banner & Witcoff, Ltd.

[57] ABSTRACT

The locus of electrically excitable tissue where action potentials are induced can be controlled using the physiological principle of electrotonus. A first pulse having a first amplitude and a first pulse width is applied to a first electrode adapted to be adjacent the tissue to generate a first subthreshold potential area within the tissue. The first subthreshold potential area is determined by the first amplitude and the first pulse width. A second pulse having a second amplitude and a second pulse width is applied to a second electrode adapted to be adjacent the tissue to generate a second subthreshold potential area within the tissue. The second subthreshold potential area is determined by the second amplitude and the second pulse width. The locus within the tissue where action potentials are induced is determined by a superposition of the first and second subthreshold areas according to the physiological principle of electrotonus. The location and size of this locus can be controlled by correspondingly adjusting at least one of the first and second amplitudes and of the first and second pulse widths or the time delay between the first and second pulses.

20 Claims, 13 Drawing Sheets

TECHNIQUES FOR ADJUSTING THE LOCUS OF EXCITATION OF ELECTRICALLY EXCITABLE TISSUE

BACKGROUND OF THE INVENTION

This is a divisional of application Ser. No. 08/814,432, filed Mar. 10, 1997, now U.S. Pat. No. 5,925,070 for which priority is claimed. This is a continuation-in-part of the earlier filed copending patent application, Ser. No. 08/627,578 filed on Apr. 4, 1996, now abandoned, U.S. Ser. No. 637,361, filed Apr. 25, 1996 now U.S. Pat. No. 5,713,922 for which priority is claimed. This parent application is incorporated herewith by reference.

FIELD OF THE INVENTION

This invention relates to means of stimulating electrically excitable tissue, and more particularly relates to means for adjusting the locus at which action potentials are induced in such tissue.

DESCRIPTION OF THE RELATED ART

Two major practical problems reduce the efficacy of epidural spinal cord stimulation (SCS) for pain control. One is the difficulty of directing the stimulation-induced paresthesia to the desired body part and the other is the problem of disagreeable sensations or motor responses to the stimulation, which reduce the comfortable amplitude range of the stimulation. It is generally agreed that in SCS, for chronic pain, paresthesia should cover the whole pain region. With present stimulation methods and equipment, only highly skilled and experienced practitioners are able to position a stimulation lead in such a way that the desired overlap is reached and desired results are obtained over time with minimal side effects. It requires much time and effort to focus the stimulation on the desired body region during surgery and, with single channel approaches, it is difficult to redirect it afterwards, even though some readjustments can be made by selecting a different contact combination, pulse rate, pulse width or voltage.

Redirecting paresthesia after surgery is highly desirable. Even if paresthesia covers the pain area perfectly during surgery, the required paresthesia pattern often changes later due to lead migration, or histological changes (such as the growth of connective tissue around the stimulation electrode) or disease progression. The problem of lead placement has been addressed by U.S. Pat. No. 5,121,754 by the use of a lead with a deformable distal shape. These problems are not only found with SCS, but also with peripheral nerve stimulation (PNS), depth brain stimulation (DBS), cortical stimulation and also muscle or cardiac stimulation.

A system capable of some adjustment of spinal cord excitation is described in PCT International Publication No. WO 95/19804 (counterpart to Holsheimer et al., U.S. Pat. No. 5,501,703). However, that system requires three electrodes, optimally spaced, which is a serious handicap during the surgical procedure required in order to place these electrodes in the body. That system steers the locus of excitation by varying the potentials between the electrodes that are optimally spaced in a line.

In fact, the electrodes in that prior art system are referred to as "in-line" electrodes that are disposed "symmetrically" along a line. The electrical field pattern across that line is adjusted by varying the electrical field generated between those electrodes along that line. The locus of excitation is correspondingly varied with that variation in the electrical field pattern.

Thus, because U.S. Pat. No. 5,501,703 to Holsheimer et al. requires multiple electrodes optimally spaced symmetrically along a line, a lead such as a paddle is used for mounting the multiple electrodes in the optimally spaced positions. This lead is then inserted within a patient near the tissue to be excited with the electrical excitation applied to the lead. Unfortunately, placement of a lead such as the paddle within a patient, can be difficult since the paddle can be surgically difficult to manipulate adjacent the spinal cord.

Thus, it would be desirable to be able to adjust the locus of excitation in electrically excitable tissue without the use of optimally spaced electrodes.

OBJECTS OF THE INVENTION

Accordingly, a primary object of the present invention is to provide a method and apparatus for adjusting the locus of excitation in electrically excitable tissue using electrodes that do not have to be optimally spaced in a line.

In particular, an object of the present invention is to adjust areas of subthreshold excitation in order to adjust an area of superposition of such areas of subthreshold excitation. The area of superposition determines the locus of excitation of electrically excitable tissue.

SUMMARY OF THE INVENTION

In a principle aspect, the present invention takes the form of an apparatus and method for inducing action potentials at an adjustable locus of electrically excitable tissue. In accordance with the invention, a first pulse having a first amplitude and a first pulse width is applied to the tissue via a first electrode adapted to be adjacent said tissue. Similarly, a second pulse having a second amplitude and a second pulse width is applied to the tissue via a second electrode adapted to be adjacent said tissue.

The application of the first pulse generates a first subthreshold potential area in said tissue, and the application of the second pulse generates a second subthreshold potential area. The first subthreshold area is determined by the first amplitude and the first pulse width of the first pulse, and the second subthreshold area is determined by the second amplitude and the second pulse width of the second pulse. A superposition of the first and second subthreshold areas results in a suprathreshold potential area of said adjustable locus where the action potentials are induced.

This embodiment of the present invention may be applied to particular advantage when adjusting the locus where the action potentials are induced. The first amplitude or the first pulse width of the first pulse can be adjusted for a corresponding adjustment of the first subthreshold area and in turn the suprathreshold potential area. Similarly, the second amplitude or the second pulse width of the second pulse can be adjusted for a corresponding adjustment of the second subthreshold area and in turn of the suprathreshold potential area The size and location of the suprathreshold potential area can thus be controlled.

In another aspect of the present invention, a time delay between the application of the first and second pulses can be varied for a corresponding adjustment in size and location of the suprathreshold potential area. The time delay between the application of the first and second pulses can be measured from the end time of the first pulse to the begin time of the second pulse. Additionally, that delay can be measured as a difference between a first weighted average time of the first pulse and a second weighted average time of the second pulse, or between a first peak time of the first pulse and a second peak time of the second pulse.

These and other features and advantages of the present invention will be better understood by considering the following detailed description of the invention which is presented with the attached drawings.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 8:
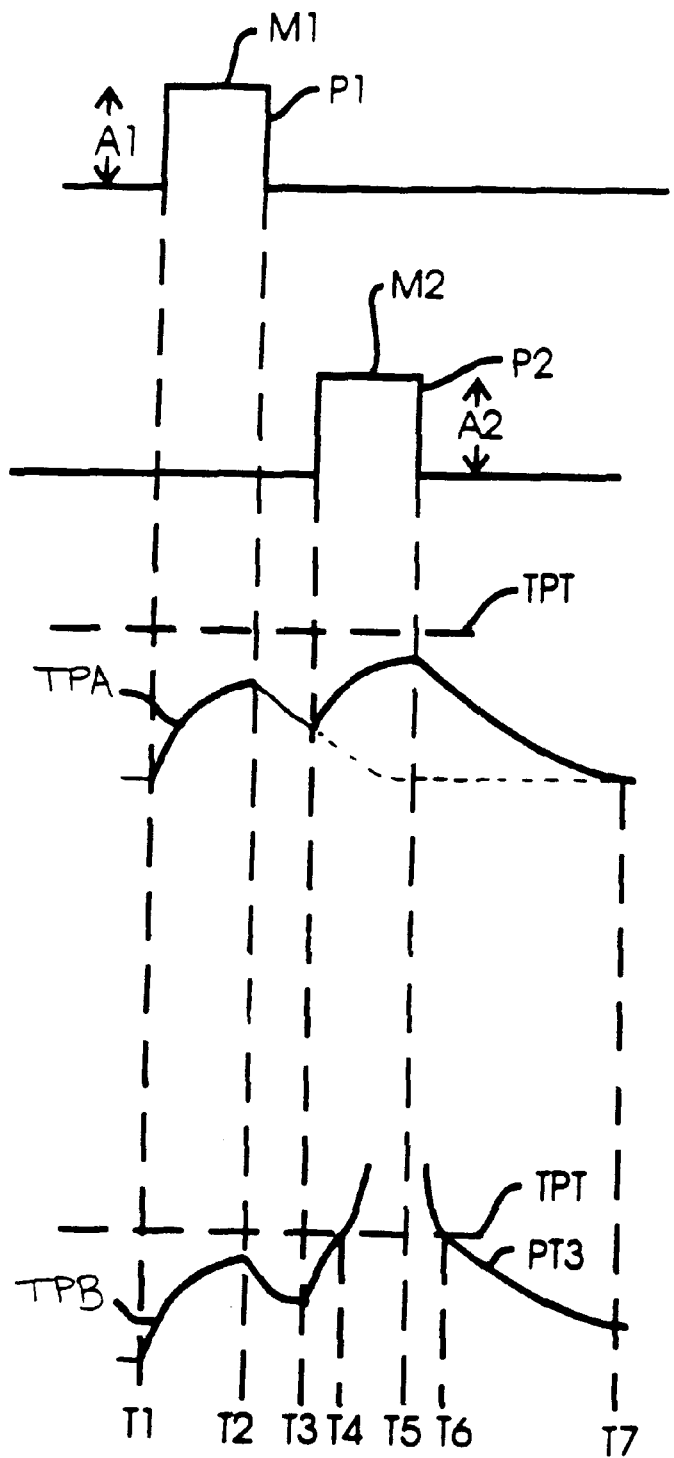
FIG. 8 is a timing diagram showing pulses applied to the first and second electrodes illustrated in FIG. 2 in relationship to the potential changes induced in tissue adjacent the electrodes.

Referring to FIG. 8, a single electrical pulse P1 can cause depolarization near a cathode in electrically excitable tissue which includes neural tissue or muscle tissue. Neural tissue includes peripheral nerves, ganglia, the spinal cord surface, deep spinal cord tissue, deep brain tissue, and brain surface tissue. Muscle tissue includes skeletal (red) muscle, smooth (white) muscle, and cardiac muscle. A locus includes a set of points in three-dimensional space and refers to a volume of cells or parts of cells. Due to the electrical characteristics of both the three-dimensional volume conductor and the membrane properties, the potentials outside and inside a neuron respond to the depolarization, usually with exponential-type increases and then attenuation overtime. The time constant for an isolated neuron membrane typically is 5–15 milliseconds (*Nerve, Muscle and Synapse* by Bernard Katz, circa 1972). For myelinated axons or muscle cells, it may be considerably shorter.

A living cell at any time has a transmembrane potential across its membrane. This transmembrane potential is typically defined as the potential in the inside of the cell with respect to the outside of the cell. At rest, a living cell has a constant transmembrane potential called a resting potential of approximately −60 mV to −90 mV, with the inside of the cell being more negative than outside of the cell. A variety of changes to the environment of the living cell can result in a corresponding change in the transmembrane potential.

A change in the environment that causes the inside of the cell to become less negative is referred to as a "depolarization" of the cell, and depolarization is then a positive change in the transmembrane potential. Similarly, a change in the environment that causes the inside of the cell to become more negative is referred to as a "hyperpolarization" of the cell, and hyperpolarization is a negative change in the transmembrane potential. An example change in the environment of a living cell is when a voltage pulse is applied near the cell. Depending on the direction of the electric current caused by this stimulation pulse, the pulse can be either depolarizing or hyperpolarizing.

FIG. 8 shows an example pulse P1 that can cause depolarization in a cell, and this depolarization from application of pulse P1 adjacent the cell can result in a transmembrane potential TPA between times T1 and T3 within the cell. A further application of another pulse P2 adjacent the cell results in a portion of the curve TPA between times T3 and T7. This portion of the curve is comprised of the superposition of the depolarization caused by pulse P2 and the remaining depolarization from the earlier application of pulse P1. This remaining depolarization from the prior application of pulse P1 is shown by the dashed line curve between times T3 and T7.

The transmembrane potential TPA between times T1 and T3 is comprised of two components. The first component is the resting potential of the cell. This component is a constant gradient that exists across the membrane of the cell. Added to that first component is the depolarization that results from the application of pulse P1. Thus, transmembrane potential TPA during time T1 and T3 is the sum total of the resting potential with the depolarization effects from application of pulse P1.

The sum total transmembrane potential TPA at any time must reach a transmembrane potential threshold in order for the electrically excitable cell to get an action potential induced therein. The peak of potential TPA is below the transmembrane potential threshold TPT, and potential TPA can be characterized as a subthreshold potential. As a result, the potential TPA fails to produce an action potential in that cell.

Action potential is an all-or-none, nonlinear phenomenon, caused by opening of sodium gates, inrush of sodium ions, and a delayed opening of potassium gates and a restoration of the membrane potential. In general, a certain amount of charge must be passed at the electrodes (amplitude [Volts]/resistance [Ohms]×pulse width [time]) in order to cause enough depolarization for an action potential to begin. There is a reciprocal relationship between amplitude and pulse width; the product must reach a certain value before the transmembrane potential threshold is reached. This relationship does not reach the Volts=0 axis. There is a certain minimum voltage needed, called rheobase, before an action potential can happen.

Basic neurophysiological principles, called "electrotonus", show that in any volume of electrically excitable tissue in which two or more depolarizing pulses tending to induce action potentials, each of which alone is insufficient to bring the cells to threshold, arrive closely together in time, at least part of their effect is additive, i.e., the memory of the first pulse is still present when the second pulse arrives. If the sum of the potentials (distorted by resistive and capacitive properties of the surroundings and the cell membranes) can get some cells depolarized to threshold, then an action potential will start in those cells. A reference that explains these principles of "electrotonus" including the creation of subthreshold potentials is *Medical Physiology*, 13th Edition, Vol. 1, by Vernon B. Mountcastle, C. V. Mosby Co., 1974.

Still referring to FIG. 8, the inducement of an action potential in a cell is illustrated by a transmembrane potential TPB reaching the transmembrane potential threshold TPT at time T4. TPB can be characterized as a suprathreshold potential, and the nerve tissue has an action potential started when TPB reaches the transmembrane potential threshold (at time T4). The transmembrane potential TPB is comprised of the constant resting potential and a depolarization that is sufficient enough to push the total transmembrane potential TPB above the transmembrane potential threshold. TPB at time T4 has sufficient depolarization to go above the transmembrane potential threshold because the amplitude of pulse P2 may have been larger than in the case of the subthreshold transmembrane potential TPA.

Figure 1:
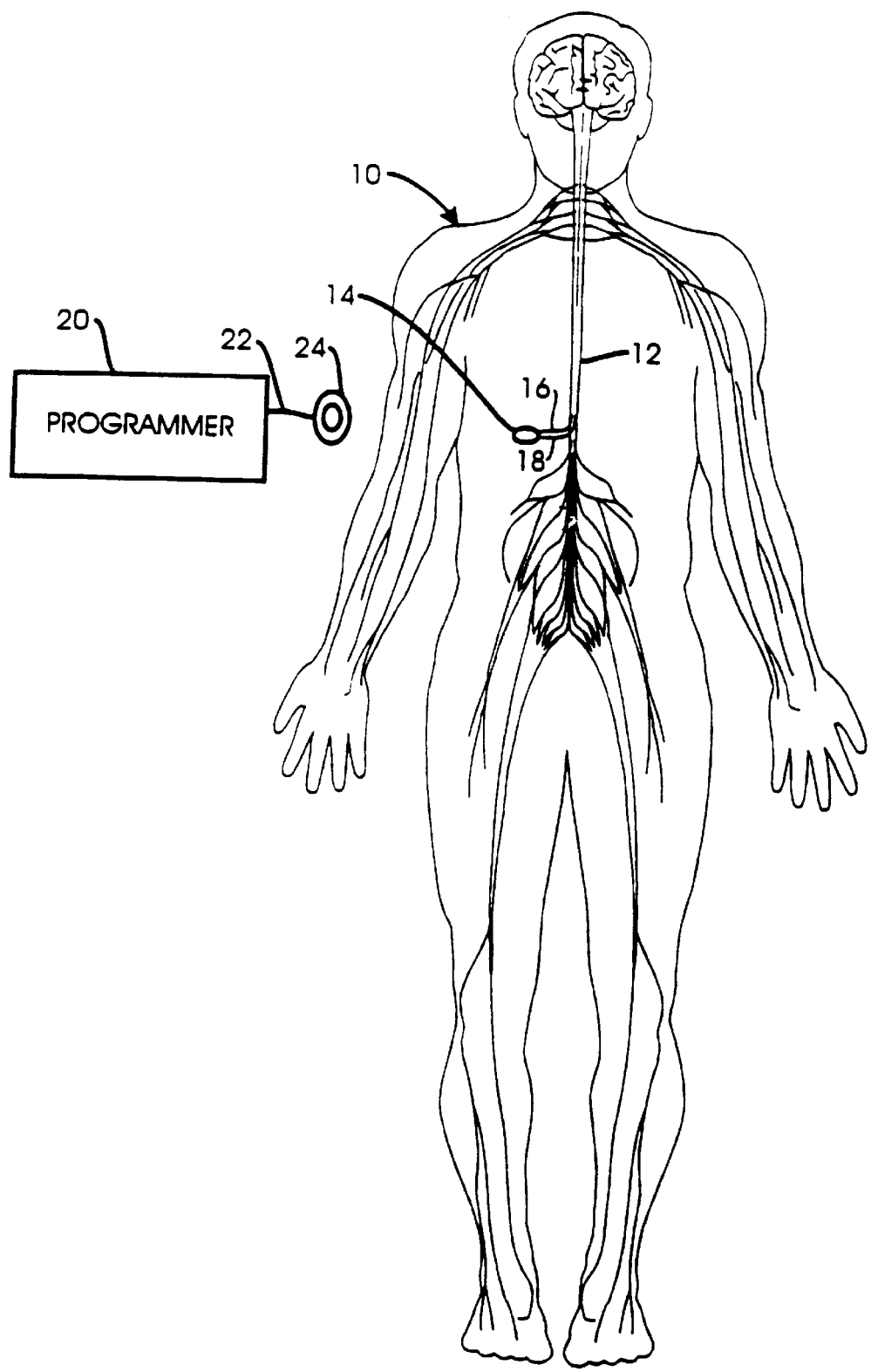
FIG. 1 is a diagrammatic view of a patient in which a preferred form of apparatus for SCS made in accordance with the invention has been implanted.
Figure 2:
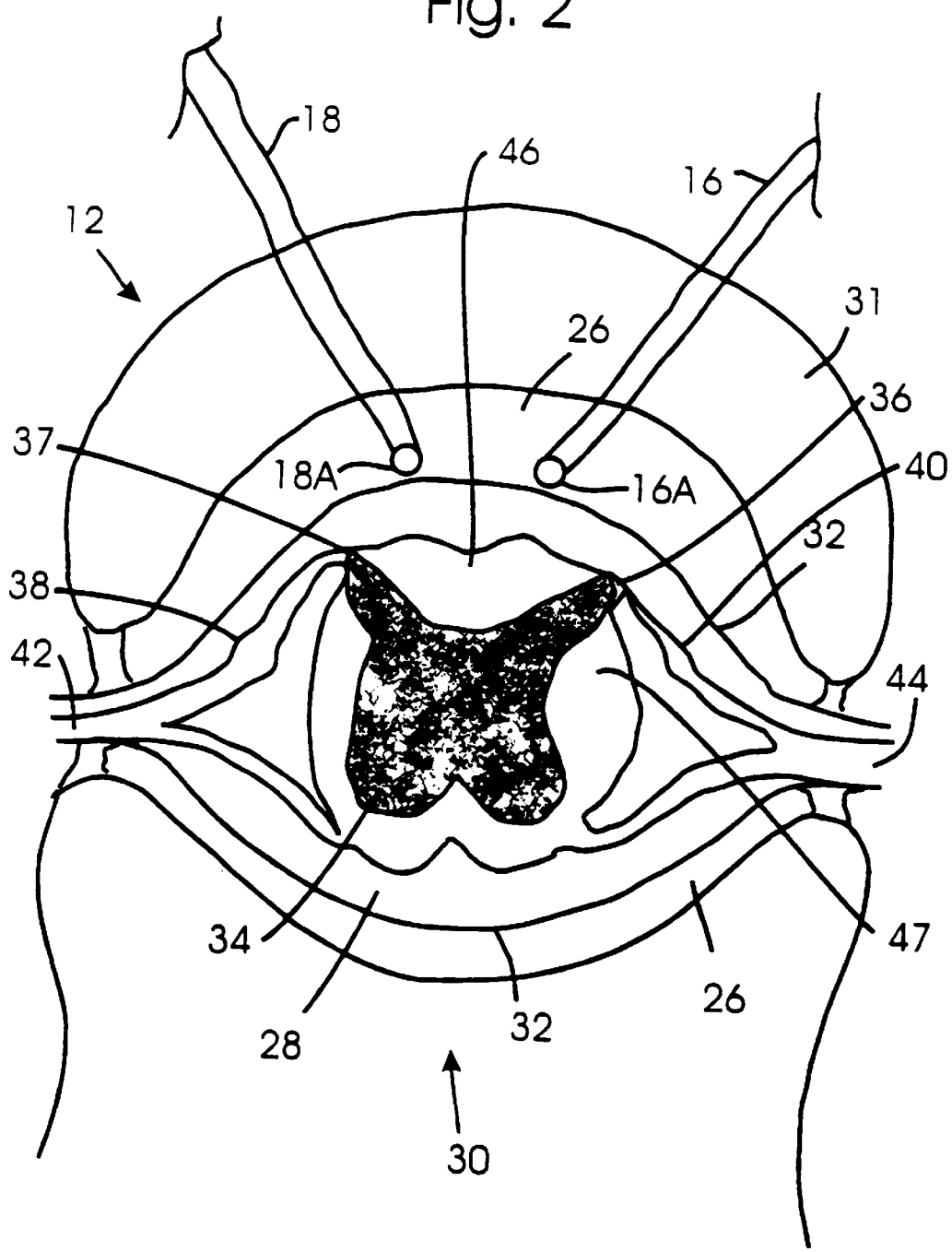
FIG. 2 is a cross-sectional view of an exemplary spinal column showing a typical position at which electrodes made in accordance with the preferred practice of the invention have been implanted in the epidural space.

FIG. 1 is a schematic view of a patient 10 having an implant of a neurological stimulation system employing a preferred form of the present invention to stimulate spinal cord 12 of the patient. The preferred system employs an implantable pulse generator 14 to produce a number of independent stimulation pulses which are sent to spinal cord 12 by insulated leads 16 and 18 coupled to the spinal cord by electrodes 16A and 18A (FIG. 2). Electrodes 16A and 18A also can be attached to separate conductors included within a single lead.

Implantable pulse generator 14 preferably is a modified ITREL II implantable pulse generator available from Medtronic, Inc. with provisions for multiple pulses occurring either simultaneously or with one pulse shifted in time with respect to the other, and having independently varying amplitudes and pulse widths. This preferred system employs a programmer 20 which is coupled via a conductor 22 to a radio frequency antenna 24. This system permits attending medical personnel to select the various pulse output options after implant using radio frequency communications. While the preferred system employs fully implanted elements, systems employing partially implanted generators and radio-frequency coupling may also be used in the practice of the present invention (e.g., similar to products sold by Medtronic, Inc. under the trademarks X-trel and Mattrix).

FIG. 2 is a cross-sectional view of spine 12 showing implantation of the distal end of insulated leads 16 and 18 which terminate in electrodes 16A and 18A within epidural space 26. The electrodes may be conventional percutaneous electrodes, such as PISCES® model 3487A sold by Medtronic, Inc. Also shown is the subdural space 28 filled with cerebrospinal fluid (cfs), bony vertebral body 30, vertebral arch 31, and dura mater 32. The spine also includes gray matter 34 and dorsal horns 36 and 37 and white matter, for example, dorsal columns 46 and dorsal lateral columns 47.

Stimulation pulses are applied to electrodes 16A and 18A (which typically are cathodes) with respect to a return electrode (which typically is an anode) to induce a desired area of excitation in the spine 12 having nerve tissue capable of producing action potentials. (A cathode has a more negative potential with respect to an anode, and the electrical current caused by the cathode tends to induce an action potential whereas the electrical current caused by the anode tends to inhibit an action potential.) The return electrode, for example a ground or other reference electrode, is also present but is not shown in the cross sectional view of spine 12 because the return electrode is located typically at a different plane from the shown cross section of FIG. 2. For example, the return electrode may be located near a point up or down the line along the spinal column 12 or at a more remote part of the body 10 carrying the spine, such as at the metallic case of the pulse generator 14. Alternatively, more than one return electrode may be present in the body. There can be a respective return electrode for each cathode such that a distinct cathode/anode pair is formed for each cathode.

Referring to FIG. 8, pulse P1 is applied to electrode 18A (FIG. 2) and pulse P2 is applied to electrode 16A (FIG. 2). Pulses P1 and P2 have a timing relationship. For optimal operation of the present invention with the application of the principle of "electrotonus", pulses P1 and P2 should not overlap in time. For example, the end of pulse P1 at time T2 and the start of pulse P2 at time T3 in FIG. 8 are displaced by a predetermined time period less than 500 microseconds, and preferably less than 50 microseconds. Amplitude A1 of P1 is adjustable independently from amplitude A2 of pulse P2. The pulse widths of pulses P1 and P2 also are independently adjustable. Widening the pulse widths of each pulse (i.e., P1 and P2) can also expand the loci of depolarizations, just like increasing amplitude, either voltage or current amplitude.

Figure 9:
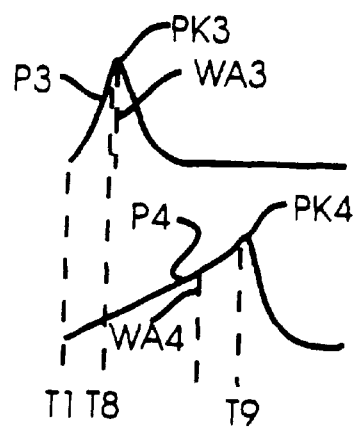
FIGS. 9 and 10 are timing diagrams illustrating alternative forms of pulses applied to the electrodes illustrated in FIG. 2.
Figure 10:
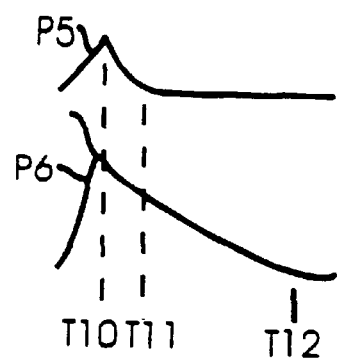

The pulses P1 and P2 also could have other time delay relationships in order to accomplish the goals of the present invention. Referring to FIG. 9, pulses P3 and P4, having different rise times, could be used. P3 has a rise time from T1 to T8 and P4 has a rise time from T1 to T9. Referring to FIG. 10, pulses P5 and P6, having different fall times, could be used. P5 has a fall time from T10 to T11, and P6 has a fall time from T10 to T12. The weighted average time WA3 of pulse P3 (FIG. 9) is displaced from the weighted average time WA4 of pulse P4 by a predetermined time period of less than 500 microseconds and preferably less than 50 microseconds. A weighted average time is the integral of a pulse over the pulse interval divided by the pulse amplitude of the pulse interval. The rise time and fall time of a pulse can affect the weighted average time of the pulse.

Similarly, the peak PK3 of pulse P3 is displaced from the peak PK4 of pulse P4 by a predetermined time period of less than 500 microseconds and preferably less than 50 microseconds. The rise time of a pulse can affect the peak time of the pulse. Objectives of the invention also can be achieved using combinations of the foregoing timing relationships. For example, the time delay between the first pulse and the second pulse can be the time difference between a first weighted average time of the first pulse and a second weighted average time of the second pulse. Alternatively, the time delay can be the time difference between a first peak time of the first pulse and a second peak time of the second pulse.

Figure 3:
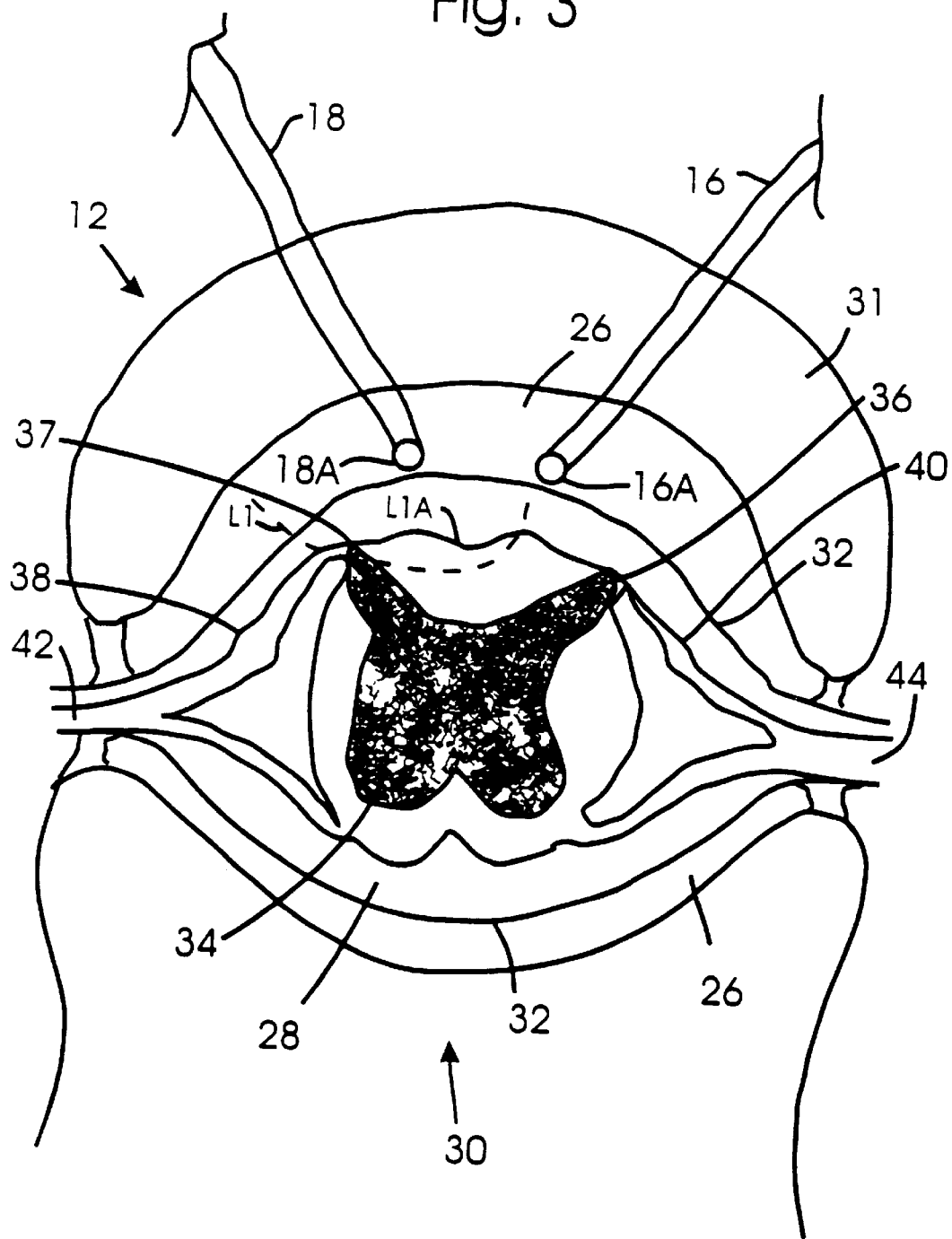
FIG. 3 is a cross-sectional view like FIG. 2 showing locus of potential changes induced in cells of the spinal cord from a pulse applied to a first one of two electrodes.

Referring to FIGS. 3 and 8, line L1 represents the edge of a three-dimensional locus L1A in which pulse P1 applied to electrode 18A results in a transmembrane potential which can be represented by the transmembrane potential curve, TPA of FIG. 8 (that part of the curve TPA between times T1 and T3 and the dashed line curve between times T3 and T7). That transmembrane potential is less than the transmembrane potential threshold TPT for cells of interest in that locus. That transmembrane potential is comprised of a constant resting potential and a depolarization caused by application of pulse P1 to electrode 18A. Thus, locus L1A, which results from pulse P1 being applied to electrode 18A without a recent pulse being applied to electrode 16A is an area having subthreshold potential since TPA is less than the transmembrane potential threshold.

Figure 4:
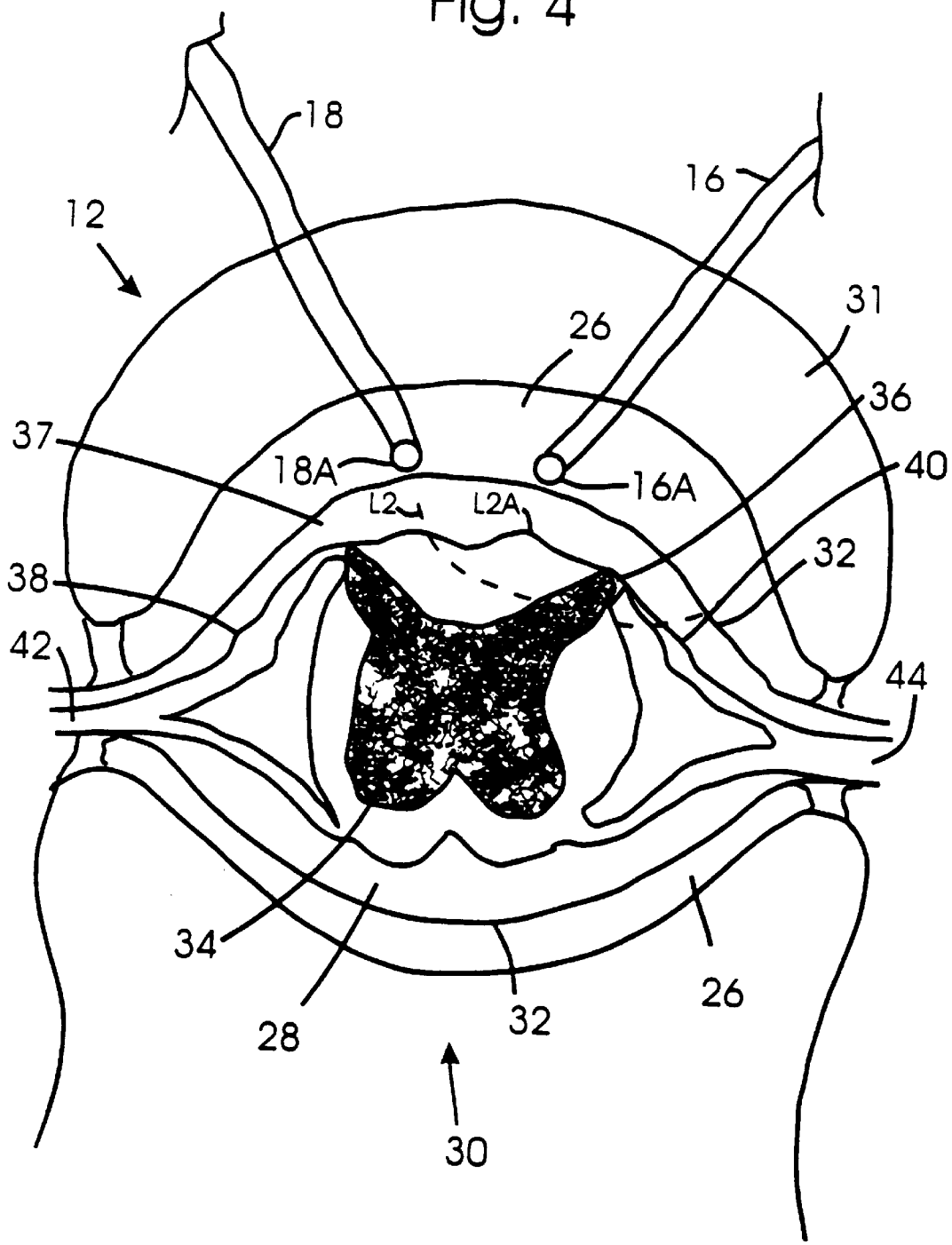
FIG. 4 is a view like FIG. 3 showing the locus of potential changes induced in cells of the spinal cord from the application of a pulse to the second of the electrodes.

Similarly, referring to FIGS. 4 and 8, line L2 represents the edge of another three-dimensional locus L2A in which the application of pulse P2 to electrode 16A results in a transmembrane potential which also can be represented by the transmembrane potential curve, TPA of FIG. 8 (that part of the curve TPA between times T1 and T3 and the dashed line curve between times T3 and T7). That transmembrane potential is less than the transmembrane potential threshold TPT for cells of interest in that locus. That transmembrane potential is comprised of a constant resting potential and a depolarization caused by application of pulse P2 to electrode 16A. Thus, locus L2A, which results from pulse P2 being applied to electrode 16A without a recent pulse being applied to electrode 18A is also an area of subthreshold potential since TPA is less than the transmembrane potential threshold.

Figure 5:
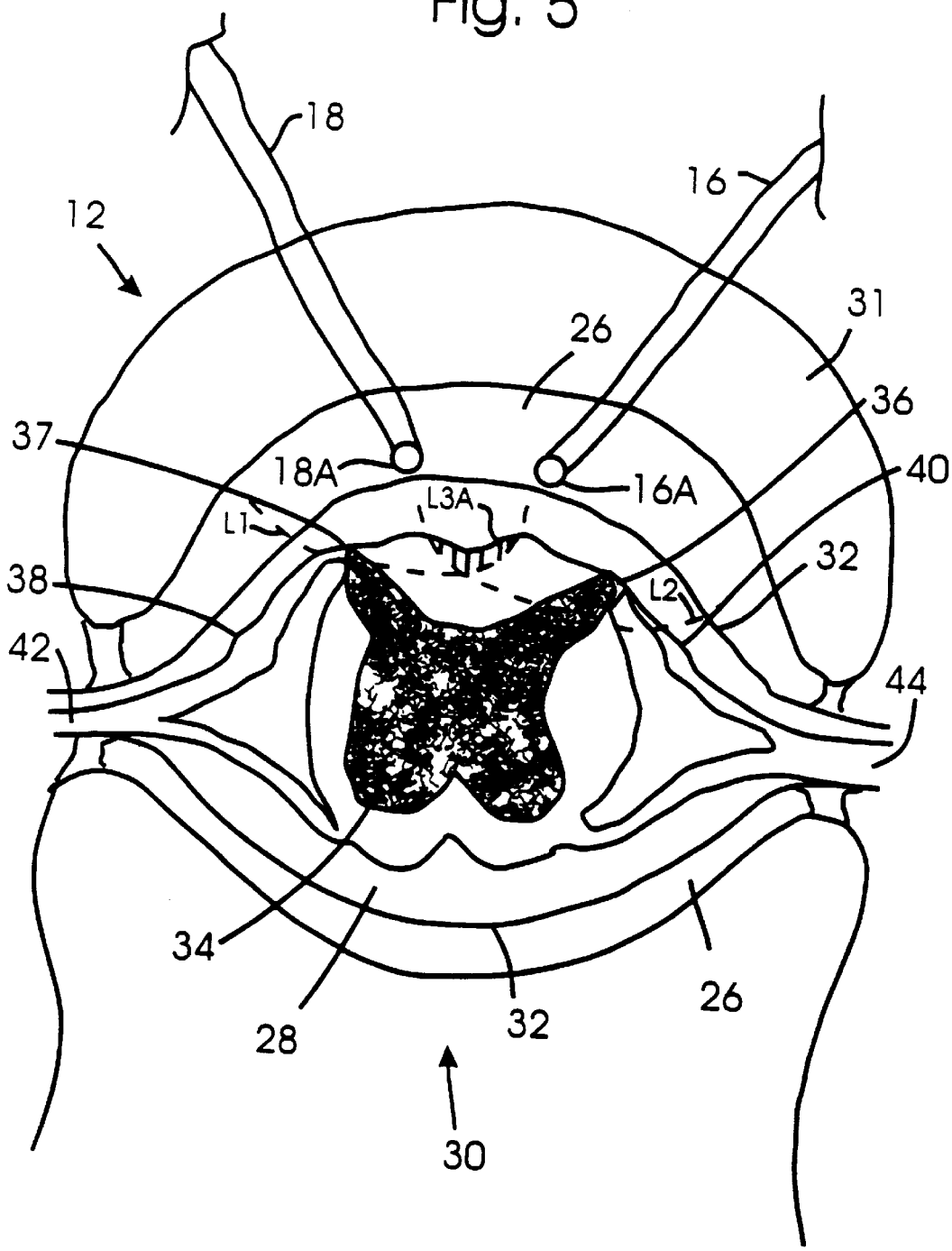
FIG. 5 is a view like FIG. 4 showing the combined loci in the spinal cord at which potential changes are induced from pulses applied to the first and second electrodes.

FIG. 5 illustrates a locus L3A representing the intersection of loci L1A and L2A in which the combined potentials induced in locus L3A from pulses P1 and P2 create an action potential in cells of interest in locus L3A as illustrated by the transmembrane potential TPB in FIG. 8. The total potential in locus L1A outside locus L3A is illustrated by the transmembrane potential TPA (that part of the curve TPA between times T1 and T3 and the dashed line curve between times T3 and T7 in FIG. 8). Since TPA is lower than the transmembrane potential threshold TPT, the total potential is a subthreshold potential, and there is no action potential created in locus L1A outside L3A. The total potential created in locus in L2A outside L3A is also illustrated by transmembrane potential TPA (that part of the curve TPA between times T1 and T3 and the dashed line curve between times T3 and T7 in FIG. 8). The total potential is a subthreshold potential, and there is no action potential created in locus L2A outside locus L3A.

The suprathreshold potential induced in locus L3A results from a superposition of the subthreshold potentials created in that area by excitation from a pulse applied to electrode 16A and from another pulse applied to electrode 18A. Locus L3A has nerve tissues that get action potentials resulting from this suprathreshold potential induced in that locus. The total potential in locus L3A is illustrated by the transmembrane potential TPB of FIG. 8. That membrane potential is comprised of the constant resting potential and the superposition of depolarizations from application of pulse P1 to electrode 18A and pulse P2 to electrode 16A.

Figure 6:
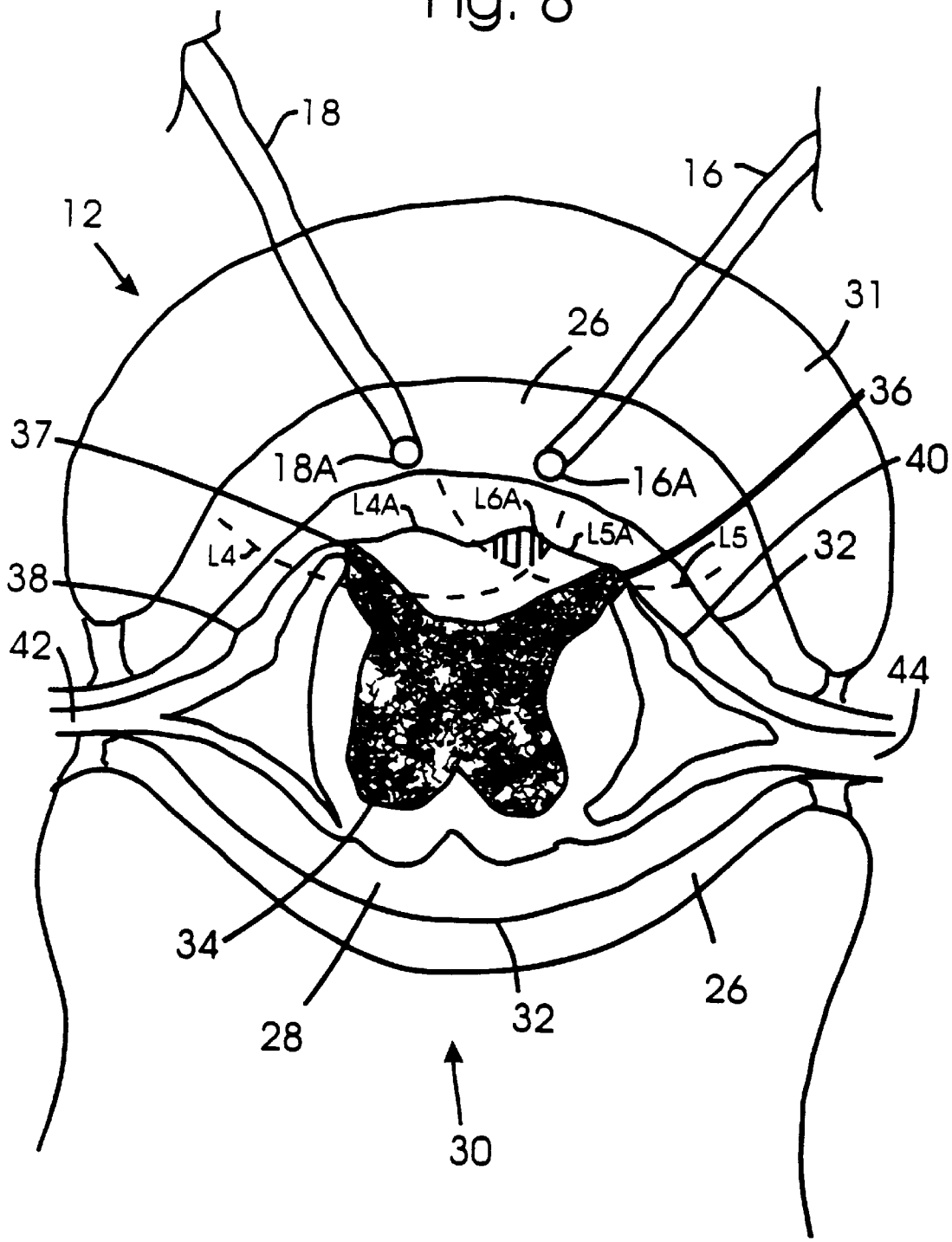
FIG. 6 is a view like FIG. 5 showing the alteration of the loci due to increase in the amplitude of the pulse applied to the first electrode and a decrease in amplitude of the pulse applied to the second electrode.

Referring to FIGS. 6 and 8, line L4 represents the edge of another three-dimensional locus L4A having subthreshold potential resulting from the application of a pulse P1 to electrode 18A having an amplitude greater than amplitude A1. Line L5 represents the edge of another three-dimensional locus L5A having subthreshold potential resulting from the application of a pulse P2 to electrode 16A having an amplitude less than amplitude A2. The intersection of loci L4A and L5A creates a locus L6A in which a suprathreshold action potential results from a superposition of subthreshold potentials created by application of pulses P1 and P2. Locus L6A is moved mostly to the right relative to locus L3A shown in FIG. 5. Action potentials are not induced outside locus L6A since the area outside that locus has subthreshold potential.

Figure 7:
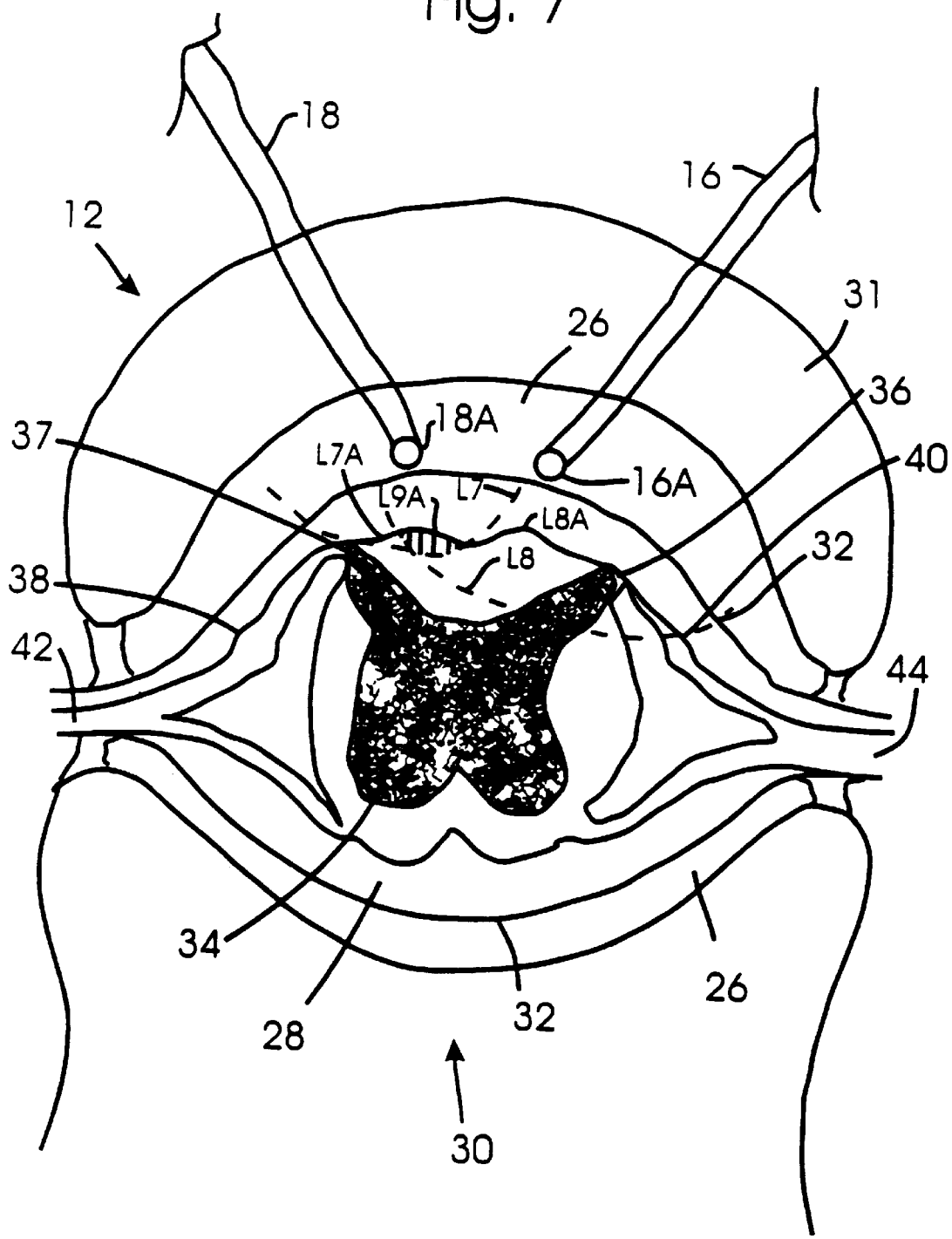
FIG. 7 is a view like FIG. 6 showing the alteration of the loci due to an increase in amplitude of the pulse applied to the second electrode and a decrease in amplitude of the pulse applied to the first electrode.

Referring to FIGS. 7 and 8, line L8 represents the edge of another three-dimensional locus L8A having subthreshold potential resulting from the application of a pulse P2 to electrode 16A having an amplitude greater than amplitude A2. Line L7 represents the edge of another three-dimensional locus L7A having subthreshold potential resulting from the application of a pulse P1 to electrode 18A having an amplitude less than amplitude A1. The intersection of loci L7A and L8A creates a locus L9A in which a suprathreshold action potential is induced from a superposition of subthreshold potentials created by application of both pulses P1 and P2. It will be noted that the locus L9A is moved to the left compared with locus L3A shown in FIG. 5. Action potentials are not induced outside locus L9A since the area outside that locus has subthreshold potential.

A benefit of utilizing the neurophysiological principle of "electrotonus" is that the area of suprathreshold potential can be controlled by varying the time delay between application of the two pulses to each respective driven electrode for creating the areas of subthreshold potential. Referring to FIG. 8, this time delay can be the time period between the end of pulse P1 at time T2 and the start of pulse P2 at time T3.

Principles of "electrotonus" indicate that a potential for any nerve cell decays with a RC time constant after a stimulation pulse has been applied to that nerve cell. R is a resistive value determined by the resistive characteristic for that nerve cell, and C is a capacitive value determined by the capacitive characteristic for that nerve cell.

Because of this memory effect of electrotonus, the transmembrane potential created within a nerve cell by a pulse starts to decay at the end of the excitation pulse, and this transmembrane potential is a function of time. By taking advantage of this time variation of the transmembrane potential, the area of suprathreshold potential can be adjusted by correspondingly varying the time delay between the pulses that are applied to two electrodes that each produce a subthreshold area.

Figure 12:
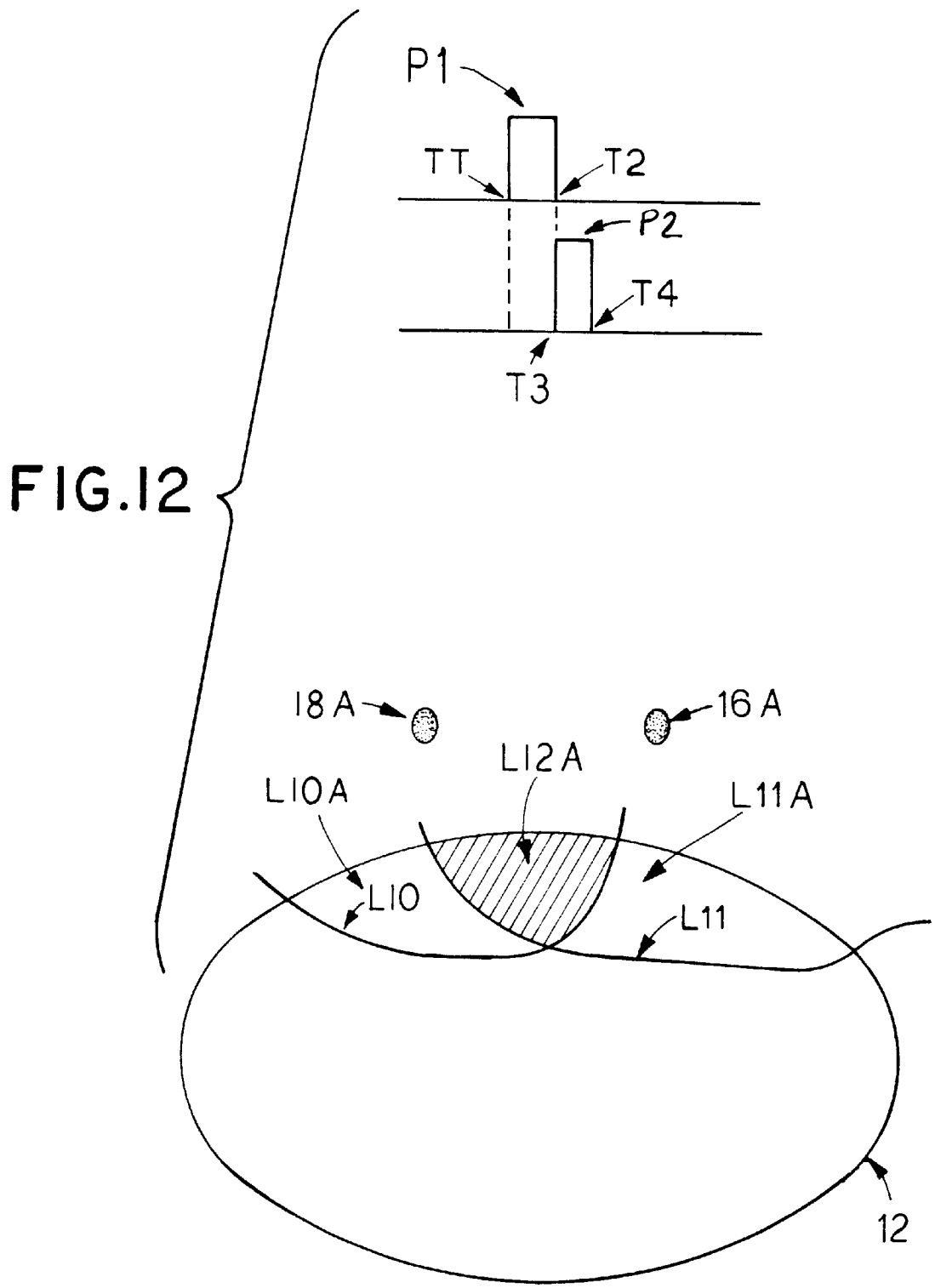
FIG. 12 shows the suprathreshold potential area generated from application of two pulses to two electrodes where the two pulses have a first time delay between the end of the first pulse and the start of the second pulse.

This benefit is further illustrated in FIGS. 12–15 where elements similar to elements in the prior figures are labeled with the same numeric label. FIG. 12 illustrates the case where the pulses applied to the two cathodes follow closely in time. Element 12 is a simplified illustration of electrically excitable tissue such as spinal column tissue. Pulse P2 immediately follows after the end of pulse P1, and the time delay between the end of pulse P1 at T2 and the start of pulse P2 at T3 is small in this case.

Figure 13:
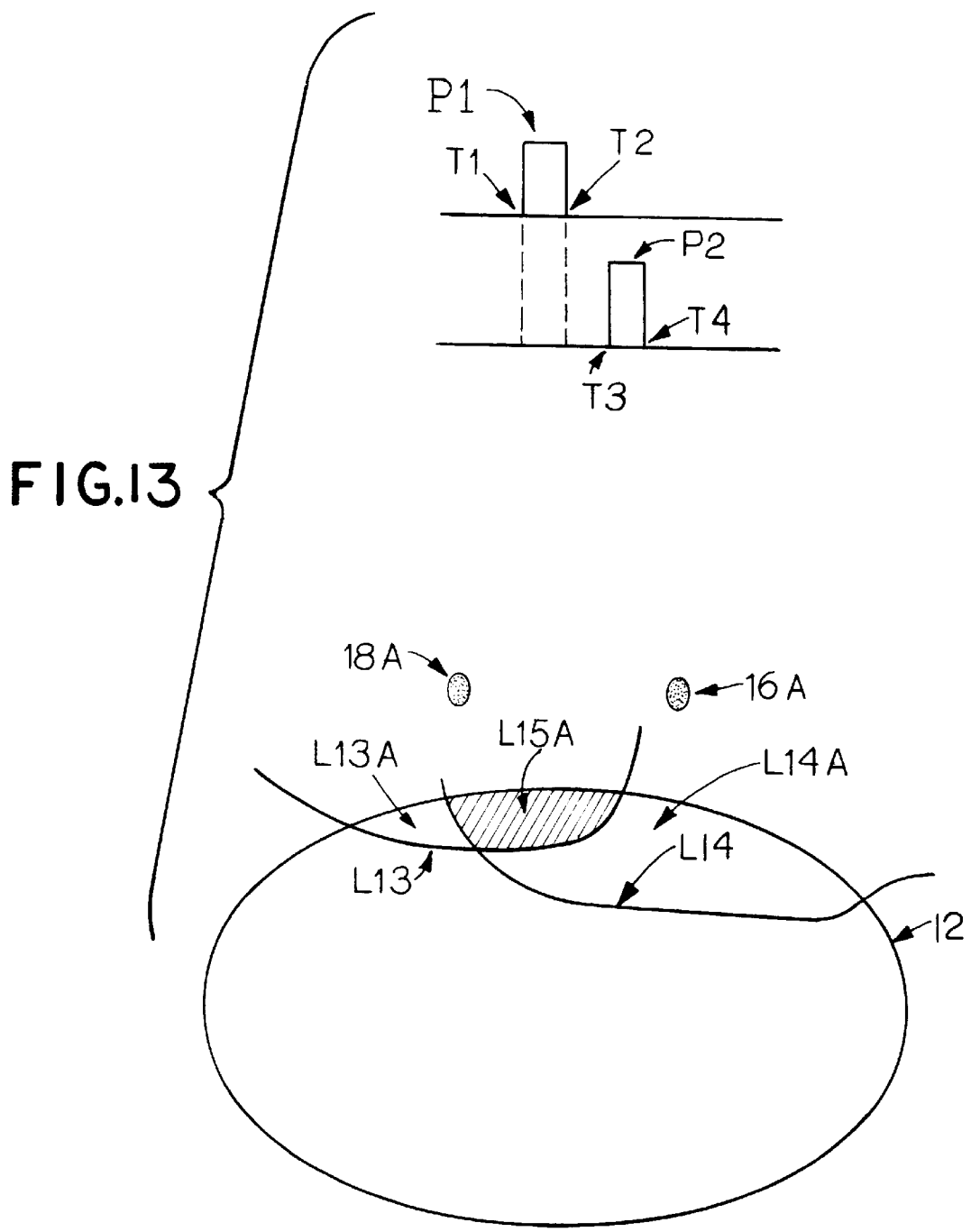
FIG. 13 shows the suprathreshold potential area generated from application of two pulses to two electrodes where the two pulses have a second time delay between the end of the first pulse and the start of the second pulse, with the second time delay being greater than the first time delay of FIG. 12.

Line L10 represents the isopotential line defining a subthreshold area L10A created by application of pulse P1 at electrode 18A. Line L11 represents the isopotential line defining another subthreshold area L11A created by application of pulse P2 at electrode 16A. (A return electrode is not shown in FIGS. 12–15 since that electrode is typically located on a different plane from the shown tissue plane 12 or on a more remote location on the body carrying the tissue 12 such as at the metallic case of the pulse generator 14 of FIG. 1.) Each isopotential line varies with time and progresses away from the electrode producing that isopotential line during the application of a pulse to that electrode and recedes back toward that electrode after the completion of the pulse by the principle of "electrotonus". In FIG. 12, the isopotential lines L10 and L11 are what result at the end of pulse P2 at time T4. These individual subthreshold areas by themselves do not have sufficient potential changes to induce an action potential within tissue 12. However, a superposition of the subthreshold potential areas at time T4 creates an area L12A of suprathreshold potential that is greater than the transmembrane potential threshold such that nerve cells within that area have an action potential induced therein. FIG. 13 shows a case where the two pulses P1 and P2 are more separated in time than the case illustrated in FIG. 12. The transmembrane potentials in FIG. 13 that are created in electrically excitable tissue 12 are those that remain at the end of pulse P2 at time T4. By that time, the application of pulse P1 was already completed at time T2. Isopotential line L13 defines the subthreshold area L13A that remains from the application of pulse P1 to electrode 18A by time T4. Isopotential line L14 defines the subthreshold area L14A that is created by application of pulse P2 to electrode 16A by time T4.

These individual subthreshold areas by themselves do not have sufficient potential changes to induce an action potential. However, a superposition of the subthreshold potential areas creates an area L15A of suprathreshold potential that is greater than the transmembrane potential threshold such that nerve cells within that area have an action potential induced therein. Note that the area of suprathreshold potential L15A of FIG. 13 differs from the area of suprathreshold potential L12A of FIG. 12 because of the larger time delay between the end of pulse P1 at T2 and the start of pulse P2 at T3 in FIG. 13 than in FIG. 12.

Figure 14:
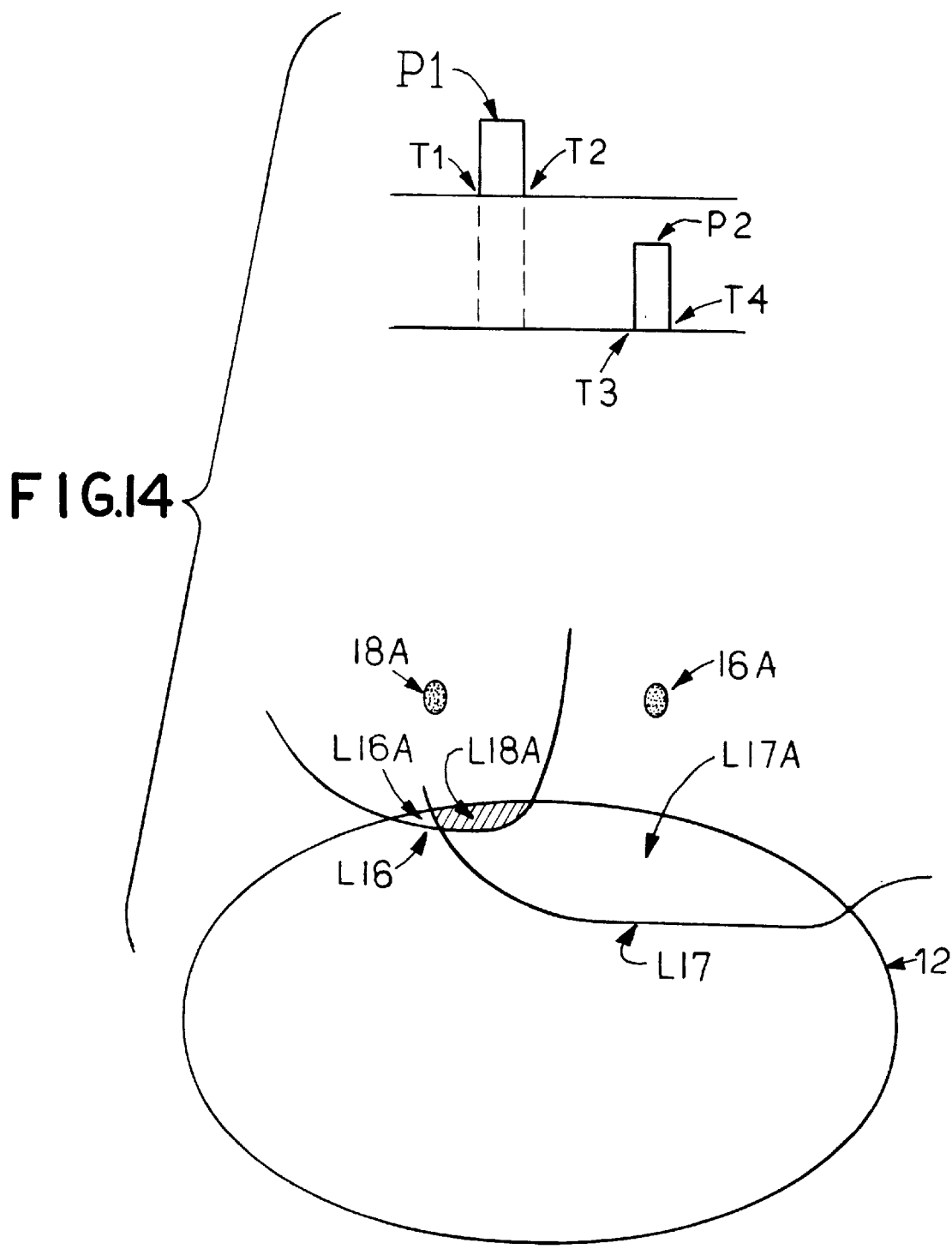
FIG. 14 shows the suprathreshold potential area generated from application of two pulses to two electrodes where the two pulses have a third time delay between the end of the first pulse and the start of the second pulse, with the third time delay being greater than the second time delay of FIG. 13.

Similarly, FIG. 14 shows a case where the two pulses P1 and P2 are still even more separated in time than those of FIG. 13. FIG. 14 shows the isopotential lines that are created by pulses P1 and P2 at the end of pulse P2 at time T4. The isopotential line L16 defines the subthreshold area L16A created by the application of pulse P1 at electrode 18A by time T4, and the isopotential line L17 defines the subthreshold area L17A created by the application of pulse P2 at electrode 16A by time T4.

The individual subthreshold areas within isopotential lines L16 and L17 by themselves do not have sufficient potential changes to induce an action potential. However, a superposition of subthreshold potential areas creates an area L18A of suprathreshold potential that is greater than the transmembrane potential threshold such that nerve cells within that area have an action potential induced therein. Note that because of the larger delay between pulses P1 and P2, isopotential line L16 has receded further toward electrode 18A by the end of pulse P2 at time T4, and the area L18A of suprathreshold potential has decreased and has shifted more toward electrode 18A.

Figure 15:
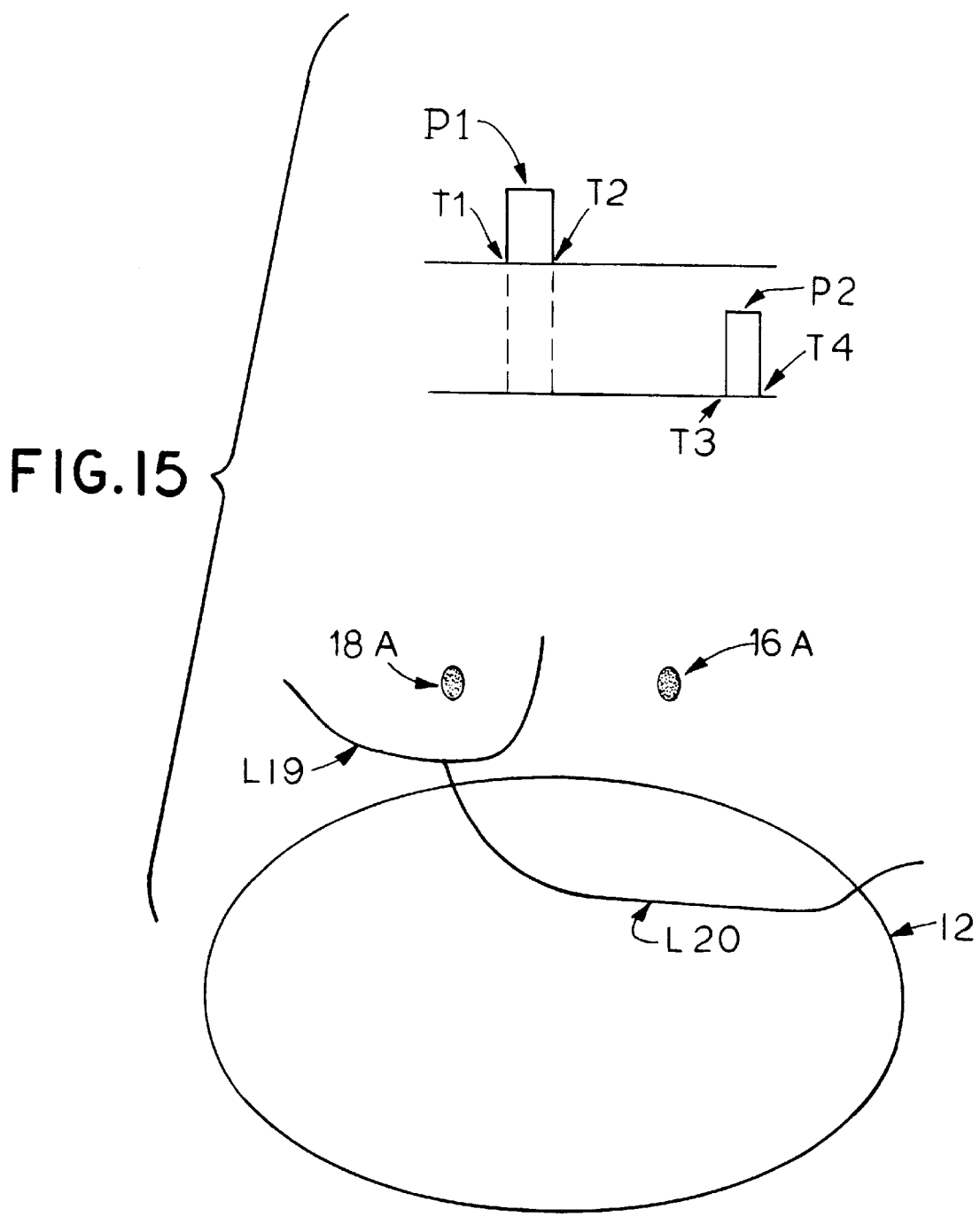
FIG. 15 shows the suprathreshold potential area generated from application of two pulses to two electrodes where the two pulses have a fourth time delay between the end of the first pulse and the start of the second pulse, with the fourth time delay being greater than the third time delay of FIG. 14.

Finally, FIG. 15 shows a case where pulse P1 and P2 have a time delay sufficiently far enough such that no area of suprathreshold potential is created within the electrically excitable tissue 12. Isopotential line L19 is the result of application of pulse P1 at electrode 18A by the end of pulse P2 at time T4, and isopotential line L20 is the result of application of pulse P2 at electrode 16A by time T4. Because of the large delay between pulses P1 and P2, isopotential line L19 has receded so far back toward electrode 18A that there is no area of superposition of the two subthreshold areas created by isopotential lines L19 and L20 within tissue 12.

The ability to move the locus in which action potentials are induced by controlling the area of superposition of subthreshold potential areas is an important feature. In many therapies, it is important to prevent action potentials being induced in gray matter 34 or dorsal horns 36 and 37, dorsal roots 38 and 40, dorsal lateral columns 47 or peripheral nerves 42 and 44 in order to minimize the possibility of causing pain, motor effects, or uncomfortable paresthesia. With the described techniques, the locus in which action potentials are induced (e.g., L3A, L6A, L9A, L12A, L15A, or L18A) can be manipulated to a desired area of the dorsal columns 46 without inducing action potentials in dorsal horns 36 and 37, gray matter 34 or dorsal lateral columns 47 or dorsal root ganglia 38 and 40. Moreover, the ability to move the locus in which action potentials are induced drastically reduces the accuracy necessary for surgically implanting electrodes 16A and 18A, and may eliminate the need for surgical lead revisions.

Another advantageous result from being able to determine the locus of excitation by controlling the area of suprathreshold potential from superposition of subthreshold potential areas is that the location of the two driven electrodes 16A and 18A and the return electrode with respect to each other is not critical to the practice of this invention. In contrast to the invention disclosed by Holsheimer et al. in U.S. Pat. No. 5,501,703, the two driven electrodes and the return electrode in the present invention are not optimally spaced in line with respect to each other. In fact, the return electrode of the present invention can be located remotely from the driven electrodes 16A and 18A near a point up or down the spinal column or another part of the body carrying the spine being excited. Alternatively, there may be more than one return electrode within the body.

Figure 11:
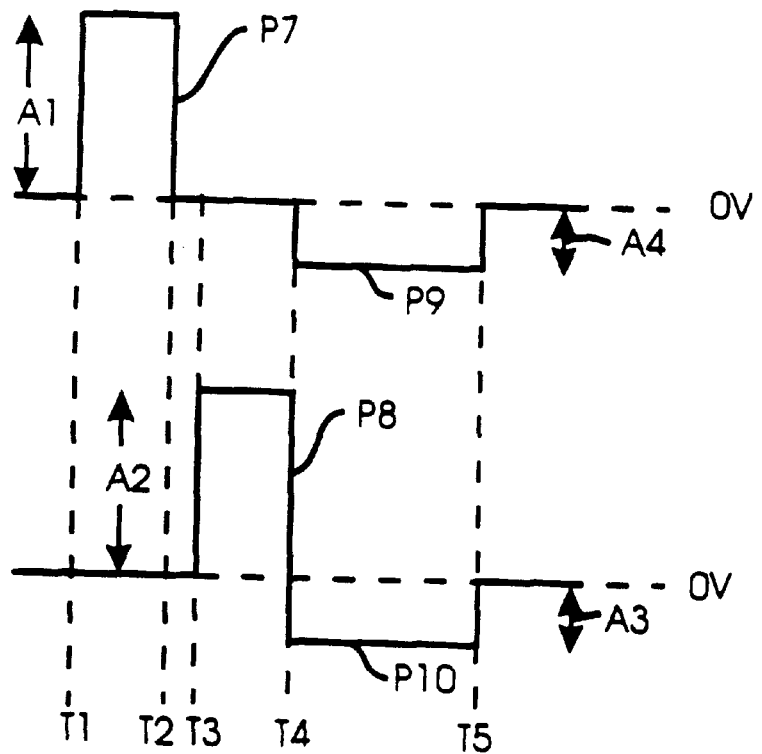
FIG. 11 is a timing diagram illustrating a preferred form of pulses applied to the electrodes shown in FIG. 2.

FIG. 11 illustrates a preferred timing relationship between pulse P7 applied to electrode 18A and pulse P8 applied to electrode 16A. Currently available pulse generators use a biphasic pulse to insure no net direct current flows into the tissue. This is known as charge-balanced pulsing, and is accomplished by driving the pulse negative for a duration of time. For example, in FIG. 11, pulse P8 has a net charge delivered proportional to A2*(T4−T3). This injected charge is balanced by the negative pulse P10, whose charge is proportional to A3*(T5−T4), where A3<<A2 and (T5−T4) >>(T4−T3). Similar principles apply even if the first and second pulses are not of constant amplitude.

In a preferred embodiment, pulse P7 may be generated with a trailing negative pulse P9 from time T4 to time T5, so that the output on electrode 18A is substantially at neutral or 0 potential until the termination of pulse P8 at time T4. Having this delay in charge balancing prevents the loss of potential in adjacent tissue that otherwise would occur if pulse P9 immediately followed pulse P7 and overlapped with pulse P8, thus offsetting the benefit of pulse P8. At time T4 both negative pulses P9 and P10 begin in order to maintain the charge balance in tissue adjacent to the respective electrodes 18A and 16A.

The advantages of the invention described herein can be generalized to applications for exciting any electrically excitable tissue within any organism, in addition to such tissue within a spine. Moreover, the invention can be generalized to using more than two cathodal electrodes to generate more than two subthreshold areas to be superposed in generating the suprathreshold potential area. Accordingly, the forgoing description is by way of example only and is not intended to be limiting. The invention is limited only as defined in the following claims and equivalents thereof.

We claim:

1. A method for inducing action potentials at an adjustable locus of electrically excitable tissue within an organism, said method including the steps of:

A. generating a first area of adjustable subthreshold potential in said tissue that results from application of a first pulse on a first cathode with respect to at least one anode, said first area of subthreshold potential emanating from and around said first cathode;

B. generating a second area of adjustable subthreshold potential in said tissue that results from application of a second pulse on a second cathode with respect to said anode, said second area of subthreshold potential emanating from and around said second cathode; and C. disposing said at least one anode within said organism where said action potentials are induced such that potential on said anode does not perturb said adjustable locus of said tissue, wherein a suprathreshold potential area is induced from a superposition of subthreshold potentials of said first and second areas in said tissue, said suprathreshold potential area being generated in between said first cathode and said second cathode wherein the step of disposing includes the step of placing said anode so that said anode is not in a line formed between said first and second cathodes.

2. The method of claim 1, further including the step of:
   adjusting a first amplitude and a first pulse width of said first pulse for a corresponding adjustment of said first area in said tissue.

3. The method of claim 1, further including the step of:
   adjusting a second amplitude and a second pulse width of said second pulse for a corresponding adjustment of said second area in said tissue.

4. The method of claim 1, further including the step of:
   adjusting a time delay between said first pulse and said second pulse for a corresponding adjustment of said adjustable locus of said tissue where said action potentials are induced.

5. The method of claim 4, wherein said time delay between said first pulse and said second pulse results in no overlap of said first pulse and said second pulse.

6. The method of claim 1, wherein the step of disposing includes the step of placing said anode in a different plane from a plane formed by said first and second cathodes.

7. The method of claim 1, wherein the step of disposing includes the step of placing said anode so that said anode is not co-linear with said first and second cathodes.

8. The method of claim 1, wherein the step of disposing includes the step of placing said anode near a point above or below a portion of a spinal column where said first and second cathodes are placed.

9. The method of claim 1, wherein the step of disposing includes the step of placing said anode at a more remote part of a body carrying a spine.

10. The method of claim 1, wherein said anode is a metallic portion of a pulse generator.

11. An apparatus for inducing action potentials at an adjustable locus of electrically excitable tissue within an organism, said apparatus comprising:

a first cathode adapted to be disposed substantially near said tissue and having a first pulse applied thereon to generate a first area of adjustable subthreshold potential in said tissue, said first area emanating from and around said first cathode;

a second cathode adapted to be disposed substantially near said tissue and having a second pulse applied thereon to generate a second area of adjustable subthreshold potential in said tissue, said second area emanating from and around said second cathode;

a generator configured to provided said first and second pulses respectively to said first and second cathodes; and at least one anode adapted to be within said organism where said action potentials are induced such that potential on said anode does not perturb said adjustable locus of said tissue wherein said anode is disposed so that said anode is not in a line formed between said first and second cathodes.

12. The apparatus of claim 11
   wherein the generator is configured to adjust a first amplitude and a first pulse width of said first pulse for a corresponding adjustment of said first area in said tissue, and adjust a second amplitude and a second pulse width of said second pulse for a corresponding adjustment of said second area in said tissue, to adjust a suprathreshold potential area of said adjustable locus of said tissue where said action potentials are induced from a superposition of subthreshold potentials of said first and second areas in said tissue, said suprathreshold potential area being generated in between said first cathode and said second cathode.

13. The apparatus of claim 11, wherein said anode is part of a metallic casing for holding said signal generator.

14. The apparatus of claim 11
   wherein the generator is configured to adjust a time delay between said first pulse and said second pulse for a corresponding adjustment of said adjustable locus of said tissue.

15. The apparatus of claim 14, wherein said time delay between said first pulse and said second pulse results in no overlap of said first pulse and said second pulse.

16. The apparatus of claim 11, said anode is adapted to be disposed in a different plane from a plane formed by said first and second cathodes.

17. The method of claim 11, wherein the step of disposing includes the step of placing said anode so that said anode is not co-linear with said first and second cathodes.

18. The apparatus of claim 11, said anode is adapted to be disposed near a point above or below a portion of a spinal column where said first and second cathodes are disposed.

19. The apparatus of claim 11, said anode is adapted to be disposed at a more remote part of a body carrying a spine.

20. The apparatus of claim 11, said anode is a metallic portion of a pulse generator.

* * * * *

UNITED STATES PATENT AND TRADEMARK OFFICE
CERTIFICATE OF CORRECTION

PATENT NO.: 6,083,252

DATED: July 4, 2000

INVENTOR(S): King et al.

It is certified that error appears in the above-identified patent and that said Letters Patent is hereby corrected as shown below:

at column 8, line 1 reads "...that membrane..." and should read - -that transmembrane- - at column 9, line 23 reads"...therein." and should read - -...therein. Fig. 13- -

Signed and Sealed this

Twenty-fourth Day of April, 2001

*Attest:*

NICHOLAS P. GODICI

*Attesting Officer*  *Acting Director of the United States Patent and Trademark Office*